United States Patent [19]

Kopp et al.

[11] Patent Number: 4,565,648
[45] Date of Patent: Jan. 21, 1986

[54] USE OF CARBONYL COMPOUNDS, SULFONYL COMPOUNDS AND/OR THIOUREAS AS STABILIZERS FOR SOLUTIONS CONTAINING PYROCARBONIC ACID DIALKYL ESTERS AND POLYISOCYANATE PREPARATIONS CONTAINING THOSE ESTERS

[75] Inventors: Richard Kopp, Cologne; Wolfgang Reichmann, Hilden, both of Fed. Rep. of Germany

[73] Assignee: Bayer Aktiengesellschaft, Leverkusen, Fed. Rep. of Germany

[21] Appl. No.: 523,300

[22] Filed: Aug. 15, 1983

[30] Foreign Application Priority Data

Aug. 24, 1982 [DE] Fed. Rep. of Germany ....... 3231397

[51] Int. Cl.$^4$ ............................................. A61K 31/265
[52] U.S. Cl. ............................... 252/397; 260/453 SP; 260/463; 514/512
[58] Field of Search ................... 252/397; 260/453 SP, 260/463; 514/512

[56] References Cited

U.S. PATENT DOCUMENTS

| | | | |
|---|---|---|---|
| 3,074,894 | 1/1963 | Loew et al. | 260/2.5 |
| 3,542,738 | 11/1970 | Stewart | 260/75 |
| 3,573,232 | 3/1971 | Kloker et al. | 260/2.5 |
| 3,584,386 | 6/1971 | Taylor | 33/205 |
| 3,751,264 | 8/1973 | Strandskov | 99/48 |
| 3,817,766 | 6/1974 | Von Bonin | 106/75 |
| 3,920,847 | 11/1975 | Chalaust | 424/301 |
| 3,936,269 | 2/1976 | Bayne | 21/58 |
| 3,985,720 | 10/1976 | Manner | 526/220 |

FOREIGN PATENT DOCUMENTS

| | | |
|---|---|---|
| 1694068 | 3/1971 | Fed. Rep. of Germany . |
| 1694069 | 3/1971 | Fed. Rep. of Germany . |
| 2053399 | 5/1972 | Fed. Rep. of Germany . |
| 2227602 | 1/1974 | Fed. Rep. of Germany . |
| 2318167 | 10/1974 | Fed. Rep. of Germany . |
| 2220564 | 10/1974 | France . |
| 1130271 | 10/1968 | United Kingdom . |

OTHER PUBLICATIONS

Chem. Abstr. 78, 3020C.
Chem. Abstr. 76, 71075h.
V. I. Kovalenko, J. Gen Chem. USSR, 1952, 22, 1587.
Chem. Abstr. 76, 13846z.
Chem. Abstr. 78, 147374u.
"Determination and Decomposition of Diethylpyrocarbonate, I. Determination with Isobutylamine and Decomposition in Various Solutions", S. Hara et al., Chemical Abstracts, vol. 67, No. 3, Jul. 17, 1967, p. 972, #10377a.

*Primary Examiner*—John Kight
*Assistant Examiner*—Marvin L. Moore
*Attorney, Agent, or Firm*—Gene Harsh; Joseph C. Gil

[57] ABSTRACT

A process for producing storage-stable solutions of pyrocarbonic acid dialkyl esters in organic liquids inert to these esters comprising adding certain carbonyl compounds, sulfonyl compounds and/or thiourea to these pyrocarbonic acid dialkyl ester solutions. Also the use of these carbonyl compounds, sulfonyl compounds and/or thiourea for producing stabilized polyisocyanate preparations suitable for the production of polyurethane foams.

4 Claims, No Drawings

USE OF CARBONYL COMPOUNDS, SULFONYL COMPOUNDS AND/OR THIOUREAS AS STABILIZERS FOR SOLUTIONS CONTAINING PYROCARBONIC ACID DIALKYL ESTERS AND POLYISOCYANATE PREPARATIONS CONTAINING THOSE ESTERS

This invention relates to the use of certain carbonyl compounds, sulfonyl compounds and/or thioureas as stabilizers for solutions containing pyrocarbonic acid dialkyl esters.

BACKGROUND OF THE INVENTION

Pyrocarbonic acid dialkyl esters corresponding to the general formula $$R-O-\underset{\underset{O}{\|}}{C}-O-\underset{\underset{O}{\|}}{C}-O-R',$$

in which R and R' may be the same or different and represent $C_1$–$C_4$, preferably $C_1$–$C_2$, alkyl radicals, more particularly pyrocarbonic acid dimethyl or diethyl esters, are used for a variety of applications. By virtue of their bactericidal and fungicidal activity, they are used, for example, for sterilizing beverages and foods (German Offenlegungsschrift No. 2,223,420, Chem. Abstr. 78 3020 c, U.S. Pat. No. 3,936,269, Chem. Abstr. 76, 71075 h). They are used in veterinary medicine for their inflammation-inhibiting effect and for their ability to accelerate the healing of wounds (German Offenlegungsschrift No. 2,307,827). Their ready decomposability under the effect of heat, optionally in the presence of special catalysts, makes them suitable for use as blowing agents in the production of foamed plastics (French Pat. No. 2,220,564, German Auslegeschriften Nos. 1,694,068 and 1,694,069 and Offenlegungsschrift No. 2,053,399) and foamed glass materials (Offenlegungsschriften Nos. 2,153,532 and 2,318,167). Further applications are, for example, their use as activators for peroxide bleaches (Offenlegungsschrift No. 2,227,602), as activators in the peroxide-catalyzed polymerization of vinyl chloride (U.S. Pat. Nos. 3,584,386 and 3,985,720), as accelerators in the production of polyesters (U.S. Pat. No. 3,542,738) and for improving the flow properties of polyurethane systems.

In storage, the above-mentioned pyrocarbonic acid esters have the property of decomposing gradually—and more quickly under the action of heat—into carbon dioxide and the corresponding dialkyl carbonate (cf., for example, V. I. Kovalenko, J. Gen. Chem. USSR 1952, 22, 1587). As a result, the concentration of solutions containing pyrocarbonic acid esters gradually decreases during storage and considerable pressure can be built up where sealed vessels are used. It is therefore of considerable interest both in terms of economy and in terms of safety to reduce or even completely suppress this decomposition of pyrocarbonic acid esters caused, in particular, by the action of heat.

It is already known that boron compounds, such as, for example, boric acid, pyroboric acid or boron trioxide, can be used for preventing the thermal decomposition of pyrocarbonic acid esters (Chem. Abstr. 76, 13846z). According to another proposal (Chem. Abstr. 78, 147374u), certain metal sulfates are added with a view to achieving the same objective. According to the teaching of these literature references, the crude product is distilled in the presence of the particular stabilizer in order thus to obtain a highly pure product in high yields. However, the particular boron and metal sulfate compounds mentioned in the cited references are insoluble in most organic solvents and, because of this, are unsuitable for the production of stabilized homogeneous solutions of the pyrocarbonic acid esters in inert organic liquids.

Accordingly, the object of the present invention is to provide effective stabilizers for pyrocarbonic acid esters or for solutions containing pyrocarbonic acid esters which are soluble in organic solvents. According to the invention, this object is achieved by the use of the carbonyl, sulfonyl or thiourea compounds described herein.

DESCRIPTION OF THE INVENTION

The present invention relates to the use of carbonyl compounds, sulfonyl compounds and/or thiourea as storability-improving additives in solutions of pyrocarbonic acid dialkyl esters in organic liquids inert to pyrocarbonic acid dialkyl esters. Suitable carbonyl, sulfonyl or thiourea compounds include those selected from the group comprising urea, N-alkyl ureas, N-aryl ureas, N,N'-diarylureas, thiourea, sulfamide, N-aryl sulfamides, N,N'-diaryl sulfamides, aliphatic or aromatic sulfonic acid amides and sulfuric acid dialkyl esters. Other such suitable compounds include aliphatic and aromatic carboxylic acid halides, aliphatic and aromatic sulfonic acid halides, aliphatic and aromatic carbonyl isocyanates, aliphatic and aromatic sulfonyl isocyanates and aliphatic and aromatic carboxylic acid anhydrides.

More particularly, the present invention is directed to a process for the production of storage-stable solutions of pyrocarbonic acid alkyl esters in organic liquids inert to these esters comprising adding to these solutions one or more carbonyl compounds, sulfonyl compounds and/or thiourea selected from the group consisting of urea, N-alkyl ureas, N-aryl ureas, N,N'-diaryl ureas thiourea, sulfamide, N-aryl sulfamides, N,N'-diarylsulfamides, aliphatic or aromatic sulfonic acid amides, sulfuric acid dialkyl esters, aliphatic and aromatic carboxylic acid halides, aliphatic and aromatic sulfonic acid halides, aliphatic and aromatic carbonyl isocyanates, aliphatic and aromatic sulfonyl isocyanates and aliphatic and aromatic carboxylic acid anhydrides.

These carbonyl compounds, sulfonyl compounds and/or thiourea are particularly suitable for the production of stabilized polyisocyanate preparations containing pyrocarbonic acid esters. Accordingly, the present invention also relates to polyisocyanate preparations suitable for the production of polyurethane foams, containing (a) at least one organic polyisocyanate which is liquid at room temperature, (b) from 0.1 to 5%, by weight, based on the polyisocyanate component, of at least one pyrocarbonic acid dialkyl ester corresponding to the formula $$R-O-\underset{\underset{O}{\|}}{C}-O-\underset{\underset{O}{\|}}{C}-O-R',$$

in which R and R' may be the same or different and represent $C_1$–$C_4$-alkyl radicals, and, (c) from 10 to 200%, by weight, based on the pyrocarbonic acid dialkyl ester component but no more than 4%, by weight, based on the mixture as a whole, of at least one carbonyl compound and/or at least one sulfonyl compound and/or thiourea of the above-mentioned type.

Stabilizers suitable for use in accordance with the invention include urea; N-alkyl ureas, particularly those containing from 1 to 4 C-atoms in the alkyl radical, such as, for example, N-methyl urea, N-ethyl urea, N-isopropyl urea, or N-(n-butyl)-urea; N-aryl ureas, particularly those containin $C_6-C_{10}$ aryl radicals, optionally having inert substituents, such as, for example, N-phenyl urea, N-(p-tolyl)-urea or N-naphthyl urea; and N,N'-diaryl ureas, particularly those containing $C_6-C_{10}$ aryl radicals optionally having inert substituents, such as, for example, N,N'-diphenyl urea, N,N'-bis-(p-tolyl)-urea, N-phenyl-N'-(p-tolyl)-urea or N-phenyl-N'-naphthyl urea. Other suitable stabilizers include thiourea; sulfamide; N-aryl sulfamides, particularly those containing $C_6-C_{10}$ aryl radicals, optionally having inert substituents, such as, for example, N-phenyl sulfamide, N-(p-tolyl)-sulfamide or N-naphthyl sulfamide; and N,N'-diaryl sulfamides, particularly those containing $C_6-C_{10}$ aryl radicals, optionally having inert substituents, such as, for example, N,N'-diphenyl sulfamide, N,N'-bis-(p-tolyl)-sulfamide or N,N'-dinaphthyl sulfamide. Aliphatic or aromatic sulfonic acid amides, particularly amides of benzene sulfonic acids, optionally containing inert substituents, such as, for example, benzene sulfonic acid amide, p-toluene sulfonic acid amide, 4-chlorobenzene sulfonic acid amide, 3-nitrobenzene sulfonic acid amide or 2-methylbenzene sulfonic acid amide, or even amides of $C_1-C_{18}$ alkane sulfonic acids, such as methane, butane or octadecane sulfonic acid amide, sulfuric acid dialkyl esters particularly containing $C_1-C_4$, and preferably $C_1-C_2$, alkyl radicals, such as dimethyl sulfate, diethyl sulfate or even di-(n-butyl)-sulfate; and aliphatic or aromatic carboxylic acid halides, particularly chlorides containing from 2 to 10 carbon atoms, such as, for example, acetyl chloride, n-propionyl chloride, benzoyl chloride, phthaloyl chloride or isophthaloyl chloride; may also be employed.

Additional suitable stabilizers include aliphatic or aromatic sulfonic acid halides, particularly chlorides containing from 1 to 10 carbon atoms, such as methane sulfonic acid chloride, butane-1-sulfonic acid chloride, benzene sulfonic acid chloride, 4-chlorobenzene sulfonic acid chloride, p-toluene sulfonic acid chloride, benzene sulfonic acid fluoride or 1,4-bis-(chlorosulfonyl)-benzene; and aliphatic or aromatic carbonyl isocyanates containing a total of from 3 to 10 carbon atoms (including the carbon atoms of the isocyanate groups), such as, for example, acetyl isocyanate, phenyl acetyl isocyanate, benzoyl isocyanate, p-nitrobenzoyl isocyanate or terephthaloyl diisocyanate. Still others include aliphatic or aromatic sulfonyl isocyanates containing a total of from 2 to 10 carbon atoms (including the carbon atoms of the isocyanate groups), such as methane sulfonyl isocyanate, benzene sulfonyl isocyanate, o- or p-toluene sulfonyl isocyanate or o- or p-chlorobenzene sulfonyl isocyanate; and aliphatic or aromatic carboxylic acid anhydrides, particularly those containing a total of 4 to 10 carbon atoms, such as, for example, acetic acid anhydride, propionic acid anhydride, succinic acid anhydride, glutaric acid anhydride or phthalic acid anhydride. Stabilizers used with particular preference in accordance with the invention are p-toluene sulfonyl isocyanate and N-phenyl sulfamide.

According to the invention, the stabilizers mentioned by way of example are used for increasing the stability in storage of solutions of pyrocarbonic acid dialkyl esters in organic liquids inert to pyrocarbonic acid esters.

The pyrocarbonic acid esters are compounds corresponding to the above formula, i.e., pyrocarbonic acid dialkyl esters containing the same or different alkyl radicals having a total of 1 to 4 carbon atoms. According to the invention, preferred pyrocarbonic acid dialkyl esters are pyrocarbonic acid diethyl and dimethyl esters.

The organic liquids inert to pyrocarbonic acid dialkyl esters, which are also present in the system to be stabilized in accordance with the invention, are preferably the usual organic solvents, such as, for example, aliphatic or aromatic hydrocarbon solvents; esters such as, for example, ethyl or butyl acetate; ketones such as, for example, methyl ethyl ketone or methyl isobutyl ketone; ether esters such as, for example, ethylene glycol monoethyl ether acetate; halogenated hydrocarbon solvents such as, for example, trichloroethane. However, the organic liquids inert to pyrocarbonic acid esters are preferably organic polyisocyanates which are liquid at room temperature and are of the type used in the production of polyurethane plastics, particularly polyurethane foams. Such polyisocyanates include, for example, 2,4- and/or 2,6-diisocyanatotoluene, 4,4'-diisocyanatodiphenyl methane liquefied by the introduction of urethane groups and/or carbodiimide groups, hexamethylene diisocyanate, urethane-group-containing NCO-prepolymers liquid at room temperature based on these polyisocyanates. Other suitable polyisocyanates include the polyhydroxyl compounds known from polyurethane chemistry which have molecular weights in the range from 62 to 6000 and, in particular, polyisocyanate mixtures which are liquid at room temperature, of the diphenyl methane series, of the type obtainable in known manner by the phosgenation of aniline/formaldehyde condensates.

The solution to be stabilized in accordance with the invention generally contains from 0.1 to 50%, by weight, based on the organic liquid, of pyrocarbonic acid dialkyl esters. The polyisocyanate preparations to be stabilized in accordance with the invention, which are suitable for the production of polyurethane foams, generally contain from 0.1 to 5%, by weight, preferably from 0.2 to 2.0%, by weight, based on the polyisocyanate component of pyrocarbonic acid dialkyl esters. The stabilizers essential to the invention are added to these solutions in quantities of at least 0.1%, by weight, based on pyrocarbonic acid esters. In the stabilization of these polyisocyanate preparations, which is the preferred application according to the invention, the stabilizers essential to the invention are generally used in quantities of from 10 to 200%, by weight, and preferably in quantities of from 10 to 60%, by weight, based on pyrocarbonic acid ester, but usually in quantities of, at most, 4%, by weight, based on the mixture as a whole. In the preparation of the solutions stabilized in accordance with the invention, the order in which the individual components are added to the system as a whole is of course immaterial.

Stabilization in accordance with the invention considerably increases the stability in storage of the solutions containing pyrocarbonic acid esters. The polyisocyanate preparations stabilized in accordance with the invention are particularly suitable for the production of polyurethane foams having an impervious outer skin (German Pat. No. 2,524,834).

In the following Examples, all the percentages quoted represent percentages by weight.

EXAMPLES

Example 1

2 g of pyrocarbonic acid dimethyl ester and 0.6 g of a stabilizer were added to batches of 200 g of freshly-distilled toluene. The samples were then stored for 21 days at 60° C. in a sealed 250 ml glass bottle.

After cooling, the pyrocarbonic acid dimethyl ester content of the individual samples was determined by gas chromatography. The results are set out in Table 1.

TABLE 1

| Stabilizer added | Residual pyrocarbonic acid dimethyl ester content after 21 days/60° C. (initial concentration: 1.0%, by weight) |
| --- | --- |
| Tosyl isocyanate | 1.0% |
| Urea | 0.5% |
| Toluene sulfonamide | 0.85% |
| N—phenyl sulfamide | 1.0% |
| None (for comparison) | 0.35% |

Example 2

2 g of pyrocarbonic acid dimethyl ester and 1 g of a stabilizer were added to batches of 200 g of a polyisocyanate mixture of the diphenyl methane series produced by phosgenating an aniline/formaldehyde condensate having an NCO-content of approximately 31% and a viscosity at 20° C. of 70–150 mPas. The samples were then stored for 21 days at 60° C. in a 250 ml glass bottle. After cooling to room temperature, the residual pyrocarbonic acid ester content was determined by IR-spectroscopy. To this end, the samples were transferred to a 0.105 mm thick sodium chloride cell and the IR-spectrum quantitatively evaluated with the aid of the pyrocarbonic acid ester absorption band at 1830 cm$^{-1}$ and a constant isocyanate absorption band at 920 cm$^{-1}$. The results are set out in Table 2.

TABLE 2

| Stabilizer added | Residual pyrocarbonic acid dimethyl ester content after 21 days/60° C. (initial concentration: 1.0%, by weight) |
| --- | --- |
| Urea | 0.68% |
| N—phenyl urea | 0.65% |
| N,N'—diphenyl urea | 0.66% |
| N—methyl urea | 0.58% |
| Thiourea | 0.55% |
| N—phenyl sulfamide | 0.71% |
| N,N'—diphenyl sulfamide | 0.35% |
| p-pyrosulfonic acid chloride | 0.65% |
| p-toluene sulfonic acid amide | 0.58% |
| p-toluene sulfonyl isocyanate | 0.65% |
| Dimethyl sulfate | 0.31% |
| Terephthaloyl chloride | 0.53% |
| Acetanhydride | 0.60% |
| None | 0.18% |

Example 3

1.7 g of pyrocarbonic acid dimethyl ester and 0.6 g of p-toluene sulfonyl isocyanate were added to 200 g of the polyisocyanate mixture of Example 2. This sample and a comparison sample which did not contain any stabilizer were each stored in sealed 250 ml glass bottles at 60° C. The pyrocarbonic acid dimethyl ester content was determined at weekly intervals by IR-spectroscopy (cf., Example 2). The results obtained are shown in Table 3.

TABLE 3

| Sample | Residual pyrocarbonic acid dimethyl ester content in %, by weight, after | | | | | | | | |
| --- | --- | --- | --- | --- | --- | --- | --- | --- | --- |
| | 0 | 1 | 2 | 3 | 4 | 5 | 6 | 7 | 8 |
| | weeks | | | | | | | | |
| With stabilizer | 0.85 | 0.77 | 0.70 | 0.64 | 0.60 | 0.52 | 0.49 | 0.45 | 0.45 |
| Without stabilizer | 0.85 | 0.53 | 0.32 | 0.17 | 0.05 | 0 | 0 | 0 | 0 |

Example 4

2 g of pyrocarbonic acid dimethyl ester and different quantities (cf., Table 4) of o-tolyl sulfonyl isocyanate were added to batches of 200 g of the polyisocyanate mixture of Example 2, followed by storage for 21 days at 60° C. in a glass bottle. Thereafter the residual pyrocarbonic acid dimethyl ester content was determined by IR-spectroscopy (cf., Example 2). The results are shown in Table 4.

TABLE 4

| Quantity of tosyl isocyanate added | Residual pyrocarbonic acid ester concentration (initial concentration: 1.0%, by weight) |
| --- | --- |
| 0 | <0.05% |
| 0.2 g | 0.32% |
| 0.4 g | 0.63% |
| 0.6 g | 0.66% |
| 1.0 g | 0.64% |

Although the invention has been described in detail in the foregoing for the purposes of illustration, it is to be understood that such detail is solely for that purpose and that variations can be made therein by those skilled in the art without departing from the spirit and scope of the invention except as it may be limited by the claims.

What is claimed is:

1. A process for the production of storage-stable solutions of pyrocarbonic acid dialkyl esters in organic liquids inert to these esters comprising adding to said esters one or more members selected from the group consisting of urea, N-alkyl ureas, N-aryl ureas, N,N'-diaryl ureas, thiourea, sulfamide, N-aryl sulfamides, N,N'-diarylsulfamides, aliphatic or aromatic sulfonic acid amides, sulfuric acid dialkyl esters, aliphatic and aromatic carboxylic acid halides, aliphatic and aromatic sulfonic acid halides, aliphatic and aromatic carbonyl isocyanates, aliphatic and aromatic sulfonyl isocyanates, and aliphatic and aromatic carboxylic acid anhydrides.

2. The process according to claim 1, wherein the pyrocarbonic acid dialkyl esters are in solutions of liquid organic polyisocyanates.

3. Polyisocyanate preparations suitable for the production of polyurethane foams, containing
(a) at least one organic polyisocyanate liquid at room temperature,
(b) from 0.1 to 5%, by weight, based on the polyisocyanate component, of at least one pyrocarbonic acid dialkyl ester corresponding to the formula

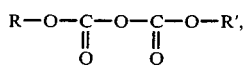

wherein R and R' may be the same or different and each represent $C_1$–$C_4$ alkyl radicals and (c) from 10 to 200%, by weight, based on the pyrocarbonic acid dialkyl ester component, but no more than 4%, by weight, based on the mixture as a whole, of at least one compound selected from the group consisting of urea, N-alkyl ureas, N-aryl ureas, N,N'-diaryl ureas, thiourea, sulfamide, N-aryl sulfamides, N,N'-diarylsulfamides, aliphatic or aromatic sulfonic acid amides, sulfuric acid dialkyl esters, aliphatic and aromatic carboxylic acid halides, aliphatic and aromatic sulfonic acid halides, aliphatic and aromatic carbonyl isocyanates, aliphatic and aromatic sulfonyl isocyanates, and aliphatic and aromatic carboxylic acid anhydrides.

4. A polyisocyanate preparation according to claim 3, characterized in that said polyisocyanate preparation contains a liquid polyisocyanate mixture of the diphenyl methane series, as component (a), a pyrocarbonic acid dimethyl ester as component (b), and p-toluene sulfonyl isocyanate or N-phenyl sulfamide as component (c).

* * * * *